United States Patent
Chen et al.

(10) Patent No.: US 9,937,116 B2
(45) Date of Patent: Apr. 10, 2018

(54) ORAL CARE WHITENING COMPOSITIONS

(71) Applicant: Colgate-Palmolive Company, New York, NY (US)

(72) Inventors: Xiang Chen, New Brunswick, NJ (US); Thomas J. Boyd, Metuchen, NJ (US)

(73) Assignee: Colgate-Palmolive Company, New York, NY (US)

( * ) Notice: Subject to any disclaimer, the term of this patent is extended or adjusted under 35 U.S.C. 154(b) by 106 days.

(21) Appl. No.: 14/443,800

(22) PCT Filed: Nov. 27, 2012

(86) PCT No.: PCT/US2012/066596
§ 371 (c)(1),
(2) Date: May 19, 2015

(87) PCT Pub. No.: WO2014/084808
PCT Pub. Date: Jun. 5, 2014

(65) Prior Publication Data
US 2015/0306001 A1  Oct. 29, 2015

(51) Int. Cl.
- *A61K 8/35* (2006.01)
- *A61K 8/22* (2006.01)
- *A61Q 11/00* (2006.01)
- *A61K 8/46* (2006.01)

(52) U.S. Cl.
CPC .............. *A61K 8/463* (2013.01); *A61K 8/22* (2013.01); *A61K 8/35* (2013.01); *A61Q 11/00* (2013.01)

(58) Field of Classification Search
USPC ........................................ 424/49
See application file for complete search history.

(56) References Cited

U.S. PATENT DOCUMENTS

| | | |
|---|---|---|
| 5,776,435 A | 7/1998 | Gaffar et al. |
| 6,030,222 A | 2/2000 | Tarver |
| 7,048,911 B2 | 5/2006 | Cashman et al. |
| 2001/0034309 A1 | 10/2001 | Shintani et al. |
| 2002/0197214 A1 | 12/2002 | Bublewitz et al. |
| 2003/0118520 A1 | 6/2003 | Reinhardt et al. |
| 2005/0163729 A1 | 7/2005 | Zaidel et al. |
| 2005/0249678 A1 | 11/2005 | Hassan et al. |
| 2005/0271602 A1 | 12/2005 | Milanovich et al. |
| 2006/0078510 A1 | 4/2006 | Takei et al. |
| 2011/0089073 A1 | 4/2011 | Baig et al. |
| 2014/0314829 A1 | 10/2014 | Boyd et al. |
| 2014/0338688 A1 | 11/2014 | Boyd et al. |

FOREIGN PATENT DOCUMENTS

| | | | |
|---|---|---|---|
| EP | 0913463 | * 6/1999 | ............... C11D 3/39 |
| GB | 2290234 | 12/1995 | |
| RU | 2283081 | 9/2006 | |

OTHER PUBLICATIONS

Iscan et al., "Antimicrobial Screening of Mentha piperita Essential Oils." J. Agric. Foof Chem. 2002, 50, 3943-3946.*
Knunyantc et al., ed., 1992, Khimicheskaya Encyclopedia, [Chemical Encyclopedia], Bolshaya Rossiiskaya Entsiklopediya vol. 3, p. 491, col. 974.
International Search Report and Written Opinion in International Application PCT/US2012/066596, dated Aug. 9, 2013.
Lide, ed., 1990, CRC Handbook of Chemistry and Physics, pp. 8-22 to 8-23.
Written Opinion in International Application PCT/US2012/066596, dated Nov. 12, 2014.

* cited by examiner

*Primary Examiner* — Walter Webb

(57) ABSTRACT

Described herein are oral care compositions comprising a whitening agent having the formula: $R^1$—O—O—$R^2$; and an aliphatic ketone; wherein $R^1$ and $R^2$ are independently selected from hydrogen, $C_1$-$C_6$ alkyl, $C_2$-$C_6$ alkenyl, $C_2$-$C_6$ carbonyl, $SO_3$, and phenyl; and methods of making and using the same.

3 Claims, No Drawings

ORAL CARE WHITENING COMPOSITIONS

BACKGROUND

Dentifrice formulations comprising various tooth whitening agents are known as being useful for cleaning and whitening teeth. A well-known tooth whitening agent is hydrogen peroxide. The hydrogen peroxide can bleach the teeth, remove stains, and kill cariogenic bacteria. In order to deliver a good whitening efficacy with an acceptable usage time, dentifrice compositions are formulated with a high peroxide content, typically above 1 wt % of the composition. However, peroxide compounds are highly reactive, and many countries have strict regulations restricting the concentration of hydrogen peroxide.

Thus, there is a need for improved single phase whitening oral care compositions, for example dentifrice compositions, which contain a whitening agent other than hydrogen peroxide and can deliver enhanced whitening performance versus known compositions.

SUMMARY

The invention at least partly aims to meet at least one of those needs.

In some embodiments, the present invention provides an oral care composition comprising a whitening agent having the formula: $R^1$—O—O—$R^2$; and an aliphatic ketone; wherein $R^1$ and $R^2$ are independently selected from hydrogen, $C_1$-$C_6$ alkyl, $C_2$-$C_6$ alkenyl, $C_2$-$C_6$ carbonyl, $SO_3$, phenyl and naphthyl.

In some embodiments, the present invention provides an oral care composition comprising a peroxodisulfate whitening agent and an aliphatic ketone.

Optionally, the peroxodisulfate whitening agent is in the form of an acid or salt thereof.

Optionally, the whitening agent is a peroxodisulfate salt selected from at least one of sodium peroxodisulfate, potassium peroxodisulfate, ammonium peroxodisulfate, lithium peroxodisulfate, calcium peroxodisulfate, and magnesium peroxodisulfate, or a mixture of any two or more of these peroxodisulfate salts.

Optionally, the whitening agent comprises sodium peroxodisulfate.

Optionally, the composition is an aqueous composition and the peroxodisulfate whitening agent is present in an amount of from 0.01M to 0.05M based on the weight of the composition.

Optionally, the composition is an aqueous composition and the peroxodisulfate whitening agent is present in an amount of from 0.1 to 10 wt % based on the weight of the composition, typically from 0.7 to 3.5 wt % or 0.24 to 1.2 wt % based on the weight of the composition.

Optionally, the composition is a substantially anhydrous composition comprising less than 5 wt % water and the peroxodisulfate whitening agent is present in an amount of from 0.1 to 45 wt %, more preferably from 0.7 to 20 wt %, more preferably from 3.5 to 10 wt % based on the weight of the composition, typically from 5 to 8 wt % or 0.24 to 1.2 wt % based on the weight of the composition.

Optionally, the aliphatic ketone is a ketone of the formula R.CO.R' where R is a $C_1$ to $C_4$ alkyl group and R' is a $C_1$ to $C_4$ alkyl group, and R and R' may be the same or different.

Optionally, R is a methyl group and R' is a $C_2$ to $C_4$ alkyl group.

Optionally, R' is an ethyl group.

Optionally, the composition is an aqueous composition and the aliphatic ketone is present in an amount of from 0.01M to 0.05M based on the weight of the composition.

Optionally, the composition is an aqueous composition and the aliphatic ketone is present in an amount of from 0.02 to 1.5 wt % based on the weight of the composition, typically from 0.05 to 0.8 wt % based on the weight of the composition.

Optionally, the composition is a substantially anhydrous composition comprising less than 5 wt % water and the aliphatic ketone is present in an amount of from 0.03 to 6 wt % based on the weight of the composition, typically from 1.3 to 4.7 wt % or 0.06 to 0.7 wt % based on the weight of the composition.

Optionally, the peroxodisulfate whitening agent and the aliphatic ketone are present in a molar ratio in the composition of from 0.5:1 to 1:0.5, further optionally from 0.75:1 to 1:0.75, still further optionally about 1:1.

Optionally, the composition is in the form of a dentifrice, a toothpaste, a mouthwash, a strip or a solid or liquid gel.

The invention also provides a method of tooth whitening comprising applying the composition of the invention to the surface of a mammalian tooth In the preferred embodiments of the invention, the oral care compositions are stable during long term storage and remain effective to clean and whiten teeth, and in addition the oral care compositions have a whitening agent which is acceptable under the regulations in force in many countries around the world.

Further embodiments of the invention will be apparent from the detailed description and the examples.

DETAILED DESCRIPTION

As used throughout, ranges are used as shorthand for describing each and every value that is within the range. Any value within the range can be selected as the terminus of the range.

Some embodiments of the present invention provide an oral care composition comprising a whitening agent having the formula: $R^1$—O—O—$R^2$; and an aliphatic ketone; wherein $R^1$ and $R^2$ are independently selected from hydrogen, $C_1$-$C_6$ alkyl, $C_2$-$C_6$ alkenyl, $C_2$-$C_6$ carbonyl, $SO_3$, phenyl and naphthyl. In some embodiments, $R^1$ and $R^2$ are $SO_3$.

In some embodiments, the present invention provides an oral care composition comprising a peroxodisulfate whitening agent and an aliphatic ketone.

In some embodiments, the peroxodisulfate whitening agent is in the form of an acid or salt thereof. Typically, the whitening agent is a peroxodisulfate salt selected from at least one of sodium peroxodisulfate, potassium peroxodisulfate, ammonium peroxodisulfate, lithium peroxodisulfate, calcium peroxodisulfate, and magnesium peroxodisulfate, or a mixture of any two or more of these peroxodisulfate salts. In one particularly preferred composition the whitening agent comprises sodium peroxodisulfate.

In some embodiments, the composition is an aqueous composition and the peroxodisulfate whitening agent is present in an amount of from 0.01M to 0.05M based on the weight of the composition and/or in an amount of from 0.1 to 10 wt % based on the weight of the composition. Typically, the composition is an aqueous composition and the peroxodisulfate whitening agent is present in an amount of from 0.24 to 3.5%, or 0.7 to 3.5 wt % or 0.24 to 1.2 wt % based on the weight of the composition.

In some alternative embodiments, the composition is a substantially anhydrous composition comprising less than 5 wt % water and the peroxodisulfate whitening agent is present in an amount of from 0.1 to 45 wt %, or 0.24 to 1.2 wt %, more preferably from 0.7 to 20 wt %, more preferably from 3.5 to 10 wt % based on the weight of the composition, typically from 5 to 8 wt % based on the weight of the composition.

The present invention is at least predicated on the finding by the inventors that by combining an aliphatic ketone with the peroxodisulfate whitening agent, the whitening efficacy of the peroxodisulfate whitening agent can be unexpectedly enhanced.

In some embodiments, the aliphatic ketone is a ketone of the formula R.CO.R' where R is a $C_1$ to $C_4$ alkyl group and R' is a $C_1$ to $C_4$ alkyl group, and R and R' may be the same or different. Typically, R is a methyl group and R' is a $C_2$ to $C_4$ alkyl group, for example an ethyl group, the ketone being methyl ethyl ketone.

In some embodiments, the composition is an aqueous composition and the aliphatic ketone is present in an amount of from 0.01M to 0.05M based on the weight of the composition and/or in an amount of from 0.02 to 1.5 wt % based on the weight of the composition. Typically, the composition is an aqueous composition and the aliphatic ketone is present in an amount of from 0.05 to 0.8 wt % based on the weight of the composition.

In some alternative embodiments, the composition is a substantially anhydrous composition comprising less than 5 wt % water and the aliphatic ketone is present in an amount of from 0.03 to 6 wt % based on the weight of the composition, typically from 1.3 to 4.7 wt % or 0.06 to 0.7 wt % based on the weight of the composition In some embodiments, the composition is an aqueous composition or a substantially anhydrous composition and the peroxodisulfate whitening agent and the aliphatic ketone are present a molar ratio in the composition of from 0.5:1 to 1:0.5, further optionally from 0.75:1 to 1:0.75, still further optionally about 1:1.

In some embodiments, the composition is in the form of a dentifrice, a toothpaste, a mouthwash, a strip or a solid or liquid gel. In some embodiments, the toothpaste may comprise an abrasive, e.g., a calcium abrasive. In other embodiments, the toothpaste may comprise an abrasive-free gel.

The compositions of the invention may optionally comprise an additional orally acceptable thickening agent, selected from one or more of, without limitation, silica, polyvinyl pyrrolidone, which may be linear or cross-linked, carbomers, also known as carboxyvinyl polymers, carrageenans, also known as Irish moss and more particularly—carrageenan (iota-carrageenan), high molecular weight polyethylene glycols (such as CARBOWAX®, available from The Dow Chemical Company), cellulosic polymers such as hydroxyethylcellulose, carboxymethylcellulose (CMC) and salts thereof, e.g., CMC sodium, natural gums such as karaya, xanthan, gum arabic and tragacanth, and colloidal magnesium aluminum silicate and mixtures of the same. Optionally, such additional thickening agents are present in a total amount of about 0.1 wt % to about 50 wt %, for example about 0.1 wt % to about 35 wt % or about 1 wt % to about 15 wt %, based on the weight of the composition.

In some embodiments, the composition further comprises polymer thickeners selected from (i) polyethylene glycol, (ii) polyethylene glycol-polypropylene glycol block co-polymers having a molecular weight of at least 5000, and (iii) combinations thereof.

In some embodiments, the composition comprises an ethylene oxide, propylene oxide block co-polymer of formula (ethylene oxide)$_x$-(propylene oxide)$_y$ wherein x is an integer of 80-150, e.g. 100-130, e.g. about 118, and y is an integer 30-80, e.g. about 60-70, e.g. about 66, having an average molecular weight of greater than 5000, e.g., 8000-13000 Da, e.g. about 9800;

In some embodiments, the composition comprises an ethylene oxide, propylene oxide block co-polymer of average molecular weight greater than 5000 Da, being substantially free of an ethylene oxide, propylene oxide block co-polymer of average molecular weight less than 5000 Da. Optionally, the ethylene oxide, propylene oxide block co-polymer is present in an amount of from 5 wt % to 10 wt % based on the weight of the composition. Block copolymers of ethylene oxide/propylene oxide are useful, but higher molecular weight, e.g., >5000 Da are preferred, e.g. including PLURACARE® L1220 (available from BASF, Wyandotte, Mich., United States of America).

In some embodiments, the composition further comprises polyethylene glycol of average molecular weight 400 to 800 Da, e.g., about 600 Da. Low or medium molecular weight polyethylene glycol, e.g., PEG 400, PEG 600, PEG 800, PEG 1000 and mixtures thereof are useful in the compositions of some embodiments of the invention.

Further optionally, the polyethylene glycol may be present in an amount of from 5 wt % to 15 wt % based on the weight of the composition.

Some embodiments further comprise an abrasive. Yet further embodiments provide oral care compositions comprising from about 5 to about 15 wt % abrasive based on the weight of the composition.

Where abrasives are present, the average particle size is generally about 0.1 to about 30 microns, for example about 1 to about 20 or about 5 to about 15 microns.

The abrasive may comprise a calcium abrasive, such as a calcium phosphate salt, e.g., calcium pyrophosphate, dicalcium orthophosphate dihydrate, tricalcium phosphate, and/or calcium polymetaphosphate. In a typical embodiment, the calcium abrasive comprises calcium pyrophosphate. In another embodiment, the calcium abrasive comprises calcium carbonate.

Optionally, the composition is a toothpaste comprising a calcium pyrophosphate abrasive. Further optionally, the calcium pyrophosphate is present in an amount of from 10 wt % to 20 wt % based on the weight of the composition.

The compositions of the invention may also comprise various dentifrice ingredients to adjust the rheology and feel of the composition such as humectants, surface active agents, or gelling agents, etc.

In some embodiments, the oral care composition comprises a vehicle for the active components. The vehicle may comprise humectants, e.g. selected from glycerin, propylene glycol or a combination thereof.

In some embodiments, the oral care composition comprises from about 20 to about 60 wt % humectant based on the weight of the composition.

In some embodiments, the composition further comprises propylene glycol in an amount of from 10 wt % to 20 wt % based on the weight of the composition.

In some embodiments, the composition further comprises glycerin in an amount of from 25 wt % to 40 wt % based on the weight of the composition.

Typical compositions of the invention may be substantially anhydrous and have a "low water" content, meaning that a total concentration of water, including any free water and all water contained in any ingredients, is less than about 5 wt %, preferably less than 3 wt %, preferably less than 2 wt % water, based on the weight of the composition.

Optionally, the composition contains less than 3 wt % water based on the weight of the composition. In some embodiments, the oral care composition contains less than 2 wt % water, e.g., less than 1 wt % water. In some embodiments, the composition is substantially anhydrous.

It is preferred that the vehicle ingredients in particular provide a dentifrice with a viscosity of about 10,000 CPS to about 700,000 CPS, preferably about 30,000 CPS to about 300,000 CPS.

As recognized by one of skill in the art, the oral compositions of the invention optionally include other materials, such as for example, anti-caries agents, desensitizing agents, viscosity modifiers, diluents, surface active agents, such as surfactants, emulsifiers, and foam modulators, pH modifying agents, abrasives, in addition to those listed above, humectants, mouth feel agents, sweetening agents, flavor agents, colorants, preservatives, and combinations thereof. It is understood that while general attributes of each of the above categories of materials may differ, there may be some common attributes and any given material may serve multiple purposes within two or more of such categories of materials. Preferably, the carrier is selected for compatibility with other ingredients of the composition.

Flavorants, sweeteners, colorants, foam modulators, mouth-feel agents and others additively may be included if desired, in the composition.

The compositions of the present invention may comprise a surface active agent (surfactant). Suitable surfactants include without limitation water-soluble salts of $C_{8-20}$ alkyl sulfates, sulfonated monoglycerides of $C_{8-20}$ fatty acids, sarcosinates, taurates, sodium lauryl sulfate, sodium cocoyl monoglyceride sulfonate, sodium lauryl sarcosinate, sodium lauryl isoethionate, sodium laureth carboxylate and sodium dodecyl benzenesulfonate, and cocoamidopropyl betaine. In some embodiments, the composition may additionally comprise a surfactant, e.g., sodium lauryl sulfate (SLS).

The compositions of the present invention optionally comprise one or more further active material(s), which is or are operable for the prevention or treatment of a condition or disorder of hard or soft tissue of the oral cavity, the prevention or treatment of a physiological disorder or condition, or to provide a cosmetic benefit.

In various embodiments of the present invention, the oral composition comprises an anticalculus (tartar control) agent. Generally, tartar control agents are categorized as being incompatible with some whitening agents, but embodiments of the present invention incorporate tartar control agents and whitening agents in a single phase whitening composition.

Suitable anticalculus agents include without limitation phosphates and polyphosphates (for example pyrophosphates), polyaminopropanesulfonic acid (AMPS), hexametaphosphate salts, zinc citrate trihydrate, polypeptides, polyolefin sulfonates, polyolefin phosphates, diphosphonates. Typically, the anticalculus agent is present at about 0.1 wt % to about 30 wt % based on the weight of the composition.

The oral composition may include a mixture of different anticalculus agents.

In some embodiments, the composition additionally comprises a tartar control agent, e.g., selected from tetrasodium pyrophosphate (TSPP) and sodium tripolyphosphate (STPP).

In one preferred embodiment, tetrasodium pyrophosphate (TSPP) and sodium tripolyphosphate (STPP) are used. The anticalculus agent comprises TSPP at about 1-2 wt % and STPP at about 7 wt % to about 10 wt %, each based on the weight of the composition.

The oral care composition can optionally include at least one orally acceptable source of fluoride ions. Any known or to be developed in the art may be used. Suitable sources of fluoride ions include fluoride, monofluorophosphate and fluorosilicate salts. One or more fluoride ion-releasing compound is optionally present in an amount providing a total of about 100 to about 20,000 ppm, about 200 to about 5,000 ppm, or about 500 to about 2,500 ppm, fluoride ions, each based on the weight of the composition.

The compositions may include a stannous ion or a stannous ion source. Suitable stannous ion sources include without limitation stannous fluoride, other stannous halides such as stannous chloride dihydrate, stannous pyrophosphate, organic stannous carboxylate salts such as stannous formate, acetate, gluconate, lactate, tartrate, oxalate, malonate and citrate, stannous ethylene glyoxide and the like. One or more stannous ion sources are optionally and illustratively present in a total amount of about 0.01% to about 10 wt %, for example about 0.1 wt % to about 7 wt % or about 1 wt % to about 5 wt %, each based on the weight of the composition.

In some embodiments, the compositions of the invention optionally comprise an antimicrobial (e.g., antibacterial) agent, e.g., triclosan. A further illustrative list of useful antibacterial agents is provided in such as those listed in U.S. Pat. No. 5,776,435 to Gaffar et al., the contents of which are incorporated herein by reference. One or more antimicrobial agents are optionally present in an antimicrobial effective total amount, typically about 0.05 wt % to about 10 wt %, for example about 0.1 wt % to about 3 wt %, each based on the weight of the composition.

In some embodiments, the compositions of the invention optionally comprise an antioxidant. Any orally acceptable antioxidant can be used, including butylated hydroxyanisole (BHA), butylated hydroxytoluene (BHT), vitamin A, carotenoids, vitamin E, flavonoids, polyphenols, ascorbic acid, herbal antioxidants, chlorophyll, melatonin, and mixtures thereof.

The compositions of the invention may optionally comprise a sialagogue or saliva-stimulating agent, an antiplaque agent, an anti-inflammatory agent, and/or a desensitizing agent.

While ingredients are sometimes identified herein by category, e.g., humectant, antioxidant, thickener, etc., this identification is for convenience and clarity, but is not intended to be limiting. All of the ingredients in the compositions may have functions in addition to their primary function, and may contribute to the overall properties of the composition, including its stability, efficacy, consistency, mouthfeel, taste, odor and so forth.

In some embodiments, the composition comprises the following ingredients by weight, each being based on the weight of the composition:

| | |
|---|---|
| Peroxodisulfate salt | 0.2 to 10%, optionally 1.5 to 3.5% |
| Aliphatic ketone | 0.03 to 6%, optionally 0.06 to 0.4% |
| Polyvinylpyrrolidone | 5-15% |
| Glycerin | 25-35% |
| Propylene glycol | 12-18% |
| Ethylene oxide, propylene oxide block co-polymer, avg. MW >5 kDa | 5-10% |
| Polyethylene glycol 600 | 5-15% |
| Calcium pyrophosphate | 10-20% |

The compositions may optionally comprise, in addition to the peroxodisulfate whitening agent, typically in an amount of 0.2-1.5 wt % or 3.5 to 10 wt %, and the aliphatic ketone whitening enhancing agent, typically in an amount of 0.06-0.4 wt % or 0.03 to 6 wt %, any or all of the following ingredient classes and/or particular ingredients by weight, each being based on the weight of the composition:

| Humectants 35-60%, e.g. | |
| --- | --- |
| Glycerin | 25-40%, e.g., about 25-35% |
| Propylene glycol | 10-20%, e.g., about 12-18% |
| Thickeners, e.g. | |
| Polyvinylpyrrolidone | 5-15%, e.g., about 8-12% |
| Polymers 10-25%, e.g., | |
| Ethylene oxide, propylene oxide block co-polymer, avg. MW >5 kDa | 5-10%, e.g., about 7-8% |
| Polyethylene glycol 600 | 5-15%, e.g., about 10% |
| Abrasive, 5-25%, e.g. | |
| Calcium pyrophosphate | 10-20%, e.g., about 15% |
| Fluoride, 0-1%, e.g. | |
| Sodium monofluorophosphate | 0.5-1%, e.g., about 0.76% |
| Surfactant, e.g., SLS | 0-3% |
| Tartar control agent, e.g. TSPP | 0.5-5%, e.g., about 2% |
| Antioxidant, 0.01-5%, e.g. | |
| BHT | 0.03% |
| Flavorings | 0.1-5% |
| Water | <3% |

The peroxodisulfate whitening agent and aliphatic ketone may be used in a whitening strip, which is formulated to be activated by water or saliva when placed against the teeth in the oral cavity. The strip may be a single layer dissolvable strip, or a two-layer strip including a rearmost backing layer for avoiding the loss of active components and a front adhesive layer formulated with the peroxodisulfate whitening agent and aliphatic ketone. Alternatively, the peroxodisulfate whitening agent and aliphatic ketone may be located at the surface of a single or two layer strip.

A single layer strip may comprise from 10 to 15 wt % of a high molecular weight homo- and/or copolymer of acrylic acid crosslinked with a polyalkenyl polyether (for example commercially available as Carbopol polymer), 50 to 60 wt % polyvinyl alcohol (PVA, commercially available as Kollicoat), 5 to 10 wt % hydroxypropyl methylcellulose, 5 to 15 wt % propylene glycol, 5 to 10 wt % Tween 80, 0.5 to 15 wt % sodium peroxodisulfate and 0.1 to 5 wt % methyl ethyl ketone.

A two layer strip may comprise, in the adhesive layer, from 10 to 15 wt % Carbopol polymer, 50 to 60 wt % polyvinyl alcohol (PVA, commercially available as Kollicoat), 5 to 10 wt % hydroxypropyl methylcellulose, 5 to 15 wt % propylene glycol, 5 to 10 wt % of a nonionic surfactant and emulsifier derived from polyethoxylated sorbitan and oleic acid (for example Polysorbate 80, commercially available as Tween 80), 0.5 to 15 wt % sodium peroxodisulfate and 0.1 to 5 wt % methyl ethyl ketone and, in the backing layer, 80 to 90 wt % polyvinyl alcohol (PVA, commercially available as Kollicoat), 5 to 15 wt % propylene glycol, and 5 to 10 wt % Tween 80.

Methods are provided to whiten an oral surface in a human or animal subject comprising storing in stable form a composition of the invention, and contacting said composition with the oral surface. As used herein "animal subject" includes higher order non-human mammals such as canines, felines, and horses. The oral care composition is contacted with an oral surface of the mammalian subject to thereby whiten teeth in a highly efficacious manner, without any negative interaction between the whitening agent, the peroxide incompatible abrasive, and other ingredients.

In various embodiments, it is preferred that the oral care composition is applied and contacted with the oral surface. The dentifrice, prepared in accordance with particular embodiments of the invention, is preferably applied regularly to an oral surface, preferably on a daily basis, at least one time daily for multiple days, but alternately every second or third day. Preferably the oral composition is applied to the oral surfaces from 1 to 3 times daily, for at least 2 weeks up to 8 weeks, from four months to three years, or more up to lifetime.

The following examples further describe and demonstrate illustrative embodiments within the scope of the present invention. The examples are given solely for illustration and are not to be construed as limitations of this invention as many variations are possible without departing from the spirit and scope thereof. Various modifications of the invention in addition to those shown and described herein should be apparent to those skilled in the art and are intended to fall within the appended claims.

EXAMPLES

Example 1

An in vitro test model is used to study the whitening performance of the combination of sodium peroxodisulfate and methyl ethyl ketone. A solution of 0.05M sodium peroxodisulfate and 0.05M methyl ethyl ketone in deionized (DI) water is prepared.

Artificially stained bovine teeth are prepared to have a starting L value between about 62 and 68, L being an indication of the whiteness of the teeth, and the baseline L, a and b values of tooth whiteness are measured, using a technique well known to those skilled in the art, using a SpectroShade™ spectrophotometer which is widely available commercially and is specifically designed to measure tooth color. This measures the initial tooth whiteness prior to a whitening treatment using the sodium peroxodisulfate/methyl ethyl ketone solution according to some embodiments of the invention.

The bovine teeth are then soaked in the sodium peroxodisulfate/methyl ethyl ketone solution for a period of 30 minutes.

The teeth are then removed from the solution and the whiteness is again measured by measuring the L*, a* and b* values using the SpectroShade™ spectrophotometer.

The increase in whiteness, expressed as $\Delta E$, is calculated from the change in the L*, a* and b* values, expressed as $\Delta L$, $\Delta a$ and $\Delta b$, and the formula $\Delta E=(\Delta L^2+\Delta a^2+\Delta b^2)$. The higher the $\Delta E$ value, the higher the increase in whiteness.

As shown in Table 1, which illustrates the value of $\Delta E$ for Example 1, $\Delta E$ was found to be 2.82. This indicates a high degree of whitening.

TABLE 1

| | $\Delta E$ |
| --- | --- |
| HP | 1.67 |
| PDS | 1.21 |
| Ketone | 0.74 |
| PDS + Ketone | 2.82 |

Comparative Examples 1, 2 and 3

The same in vitro test model of Example 1 is used to study the whitening performance of the following solutions: for Comparative Example 1 a solution of 0.05M sodium peroxodisulfate, for Comparative Example 2 a solution of 0.05M methyl ethyl ketone in deionized (DI) water and for Comparative Example 3 a solution of 0.05M hydrogen peroxide in deionized (DI) water.

The corresponding values of ΔE were calculated for each of Comparative Examples 1 to 3. As also shown in Figure 1, which illustrates the value of ΔE for Comparative Examples 1 to 3, for Comparative Example 1 ΔE was found to be 1.21, for Comparative Example 2 ΔE was found to be 0.74, and for Comparative Example 3 ΔE was found to be 1.67.

A comparison of the results of Example 1 and for Comparative Examples 1 and 2 show that the combination of sodium peroxodisulfate and methyl ethyl ketone unexpectedly provided a significant and synergistic increase in whitening, as expressed by ΔE, as compared to the individual components. The whitening efficacy of the aliphatic ketone when used alone was poor, but the aliphatic ketone significantly enhanced the whitening efficacy of the peroxodisulfate whitening agent.

Furthermore, these results of Example 1 and for Comparative Example 3 show that the combination of sodium peroxodisulfate and methyl ethyl ketone unexpectedly provided a significant increase in whitening as compared to an equivalent amount of hydrogen peroxide as whitening agent.

Example 2 and Comparative Example 4

A substantially anhydrous dentifrice is prepared according to Example 2. The composition has the following ingredients as specified in Table 1, in which the amounts are in wt %.

TABLE 1

| Ingredient | Example 2 | Comparative Example 4 |
|---|---|---|
| PEG$_{118}$/PPG$_{66}$ co-polymer (Pluracare L1220F) | 7.5 | 7.5 |
| Glycerin | 28 | 33.36 |
| Propylene glycol | 15 | 15 |
| PEG 600 | 10 | 10 |
| Sodium hydroxide (50 wt % solution) | 2 | — |
| PVP | 10 | 6 |
| Sodium peroxodisulfate | 7.14 | — |
| Crosslinked PVP/H$_2$O$_2$ | — | 5.5 |
| Methyl ethyl ketone | 2 | — |
| Calcium pyrophosphate | 15 | 15 |
| TSPP | — | 2 |
| Sucralose | — | 0.05 |
| Sodium saccharin | 0.6 | 0.6 |
| Sodium monofluorophosphate | 0.76 | 0.76 |
| Sodium lauryl sulfate | 2 | 2 |
| BHT | — | 0.03 |
| 85 wt % syrupy phosphoric acid | — | 0.2 |
| Flavor | 2 | 2 |
| Total | 100 | 100 |

Since the dentifrice of Example 2 is substantially anhydrous, a higher concentration of peroxodisulfate whitening agent can be used without a problem of excessive premature decomposition.

Example 3

An in vitro test model is again used to study the whitening performance of the combination of sodium peroxodisulfate and methyl ethyl ketone using different molar concentrations.

Composition (a) comprised a solution of 0.01M sodium peroxodisulfate and 0.01M methyl ethyl ketone in deionized (DI) water.

Composition (b) comprised a solution of 0.01M sodium peroxodisulfate and 0.05M methyl ethyl ketone in deionized (DI) water.

Composition (c) comprised a solution of 0.05M sodium peroxodisulfate and 0.01M methyl ethyl ketone in deionized (DI) water.

Composition (d) comprised a solution of 0.05M sodium peroxodisulfate and 0.05M methyl ethyl ketone in deionized (DI) water.

Artificially stained bovine teeth are prepared to have a starting L value between about 62 and 68, L being an indication of the whiteness of the teeth, and the baseline L, a and b values of tooth whiteness were measured, using the SpectroShade™ spectrophotometer. This measures the initial tooth whiteness prior to a whitening treatment using the sodium peroxodisulfate/methyl ethyl ketone solution according to the invention.

The bovine teeth are then soaked in each of the four sodium peroxodisulfate/methyl ethyl ketone solutions (a), (b), (c) and (d) for a period of 30 minutes.

The teeth are then removed from the respective solution and the whiteness is again measured by measuring the L, a and b values using the SpectroShade™ spectrophotometer.

The increase in whiteness, expressed as ΔW, is calculated from the change in the L, a and b values, expressed as ΔL, Δa and Δb, and the formula for the initial and final whiteness W values, where $W=\sqrt{(a^2+b^2+(L-100)^2)}$. The more negative the ΔW value, the higher the whitening effect.

Table 2 illustrates the value of ΔW for each of compositions (a), (b), (c) and (d).

TABLE 2

| Composition | ΔW |
|---|---|
| (a): 0.01M sodium peroxodisulfate + 0.01M methyl ethyl ketone | −0.59 |
| (b): 0.01M sodium peroxodisulfate + 0.05M methyl ethyl ketone | 0.02 |
| (c): 0.05M sodium peroxodisulfate + 0.01M methyl ethyl ketone | −0.51 |
| (d): 0.05M sodium peroxodisulfate + 0.05M methyl ethyl ketone | −0.85 |

It may be seen that for compositions (a) and (d), when both the sodium peroxodisulfate and the methyl ethyl ketone have the same molar concentrations (0.01M for composition (a) or 0.05M for composition (d)) the bovine teeth experienced a greater increase in whiteness. This indicates that with the particularly preferred molar ratio of 1:1 and molar concentrations for both the sodium peroxodisulfate and the methyl ethyl ketone of from 0.01M to 0.05M, the methyl ethyl ketone enhances the whitening efficacy of the sodium peroxodisulfate.

While particular embodiments of the invention have been illustrated and described, it will be obvious to those skilled in the art that various changes and modifications may be made without departing from the scope of the invention as defined in the appended claims.

What is claimed is:

1. An oral care composition comprising
a whitening agent, wherein the whitening agent is a sodium peroxodisulfate; and
an aliphatic ketone;
wherein the composition is an aqueous composition and the aliphatic ketone is present in a concentration of from 0.01M to 0.05M based on the weight of the composition; and
wherein the peroxodisulfate whitening agent is present in an amount of from 0.01M to 0.05M based on the weight of the composition;
wherein said aliphatic ketone is methyl ethyl ketone; and
wherein the peroxodisulfate whitening agent and the aliphatic ketone are present in a molar ratio in the composition of about 1:1.

2. The composition of claim 1 which is in a form selected from a toothpaste, a mouthwash, a strip and a solid or liquid gel.

3. A method for whitening a tooth comprising applying the composition of claim 1 to the surface of a mammalian tooth.

* * * * *